United States Patent [19]

Saeva et al.

[11] Patent Number: 5,141,969
[45] Date of Patent: Aug. 25, 1992

[54] ONIUM SALTS AND THE USE THEREOF AS PHOTOINITIATORS

[75] Inventors: Franklin D. Saeva, Webster, N.Y.; David T. Breslin, Austin, Tex.

[73] Assignee: Eastman Kodak Company, Rochester, N.Y.

[21] Appl. No.: 419,245

[22] Filed: Oct. 10, 1989

Related U.S. Application Data

[63] Continuation-in-part of Ser. No. 273,788, Nov. 21, 1988, abandoned.

[51] Int. Cl.⁵ .................. G03C 1/492; C08F 2/46; C08T 3/28
[52] U.S. Cl. ......................... 522/31; 522/25; 430/914; 430/281; 430/270; 430/280
[58] Field of Search ............ 430/914, 280, 270, 281; 522/31, 25

[56] References Cited

U.S. PATENT DOCUMENTS

| | | | |
|---|---|---|---|
| 4,026,705 | 5/1977 | Crivello et al. | 96/27 |
| 4,069,054 | 1/1978 | Smith | 96/115 |
| 4,069,055 | 1/1978 | Crivello | 96/115 |
| 4,442,197 | 4/1984 | Crivello | 430/280 |
| 4,933,377 | 6/1990 | Saeva et al. | 430/914 X |
| 4,954,416 | 9/1990 | Wright et al. | 522/31 X |
| 5,047,568 | 9/1991 | Angelo et al. | 522/31 X |

OTHER PUBLICATIONS

*Research Disclosure*, vol. 289, May 1988, p. 298, published by Kenneth Mason Publications, Ltd., London, England.

*Primary Examiner*—Cynthia Hamilton
*Attorney, Agent, or Firm*—Ogden H. Webster; Robert L. Walker

[57] ABSTRACT

Sulfonium, selenonium, arsonium, ammonium and phosphonium salts, useful as photoinitiators, comprise:

a chromophore which absorbs visible radiation, the chromophore (1) having a removable positive hydrogen ion and (2) exhibiting a higher energy occupied molecular orbital than at least one other substituent attached to the S, Se, As, N or P atom of the salt;

an insulating group which links the chromophore to the S, Se, As, N or P atom of the salt, the insulating group essentially preventing $\pi$ resonance between the chromophore and the other substituents in the salt;

at least one substituent comprising an electron withdrawing group and exhibiting a lower unoccupied molecular orbital than the chromophore; and, an anion;

the salts being capable, upon exposure to visible radiation, of forming a Bronsted acid.

17 Claims, No Drawings

ONIUM SALTS AND THE USE THEREOF AS PHOTOINITIATORS

This application is a continuation-in-part of our earlier filed application Ser. No. 273,788, filed on Nov. 21, 1988 now abandoned.

This invention relates to certain novel onium salts and, more particularly, to light sensitive onium salts. It also relates to the use of such salts as photoinitiators.

It is well known that various onium salts, upon exposure to radiation, are capable of forming a Bronsted acid, and that the Bronsted acid thus formed can cure a wide variety of materials. See, for example, *UV Curing: Science and Technology*, edited by S. Peter Pappas and published (1978) by Technology Marketing Corporation, 64 Westover Road, Stamford, Conn. 06902. The problem with such salts is that they do not absorb visible radiation, and commonly must be used in combination with a light-absorbing photosensitizer in order to carry out visible light, e.g., laser, induced photoinitiation.

*Research Disclosure* Vol. 289, May 1988, page 298, published by Kenneth Mason Publications Ltd., London, England, describes sulfonium salts and oxysulfonium salts which, upon exposure to visible radiation, undergo irreversible intramolecular rearrangement to form a Bronsted acid. The light-absorbing capability of these sulfonium and oxysulfonium salts depends upon resonance (i.e., $\pi$ resonance) throughout the molecule. The photo products of these salts absorb at shorter wavelengths than the starting sulfonium and oxysulfonium salts.

There is a need in the art for onium salts which absorb visible radiation by means of a chromophore joined, through an insulating linkage, to the remainder of the molecule. Such salts should be capable of forming a Bronsted acid upon exposure of the light absorbing chromophore to visible light. The advantage of such salts is that a chromophore could be selected which matches the desired exposing radiation, such as a visible laser, e.g., argon ion (488/515 nm), nitrogen ion (423 nm), copper vapor (510/578 nm), e-beam pumped CdS (494 nm) and the He-Ne laser 632 nm.

Onium salts having the desired properties described above are provided in accordance with this invention and include sulfonium, selenonium, arsonium, ammonium and phosphonium salts comprising:

a chromophore which absorbs visible radiation, said chromophore exhibiting a higher energy occupied molecular orbital than at least one other substituent attached to the S, Se, As, N or P atom of said salt;

an insulating group which links said chromophore to the S, Se, As, N or P atom of said salt, said insulating group essentially preventing $\pi$ resonance between said chromophore and the other substituents in said salt;

at least one substituent comprising an electron withdrawing group and exhibiting a lower unoccupied molecular orbital than said chromophore; and, an anion;

said salt being capable, upon exposure to visible radiation, of forming a Bronsted acid.

The onium salts of this invention comprise a chromophore, i.e., a covalently unsaturated group responsible for electronic absorption, and which absorbs visible light. The chromophore is chemically linked to the remainder of the salt by an insulating group which essentially prevents $\pi$ resonance between the chromophore and the rest of the salt. As used herein, "essentially insulating" means that the salt formed exhibits a shift in absorbance of no more than about 30 nm, and preferably less than 15 nm. Preferably, the chromophore is non-basic and the conjugate acid has a pKa of from 0 to −20. Advantageously, the chromophore has a hydroxy, nitrile, carbonyl or carboxy group, or an ether or ester group which in its protonated form would be a strong acid as previously defined.

The preferred onium salts of this invention are sulfonium salts. Arsonium and selenonium salts are also highly useful. Sulfonium, selenonium and arsonium salts can be used without a separate proton source material, such as water, an amine or an alcohol. Such proton source materials are employed when the onium salt is an ammonium or phosphonium salt. When the ammonium and phosphonium salts of this invention are exposed to visible radiation, an intermolecular reaction occurs which results in the formation of a Bronsted acid comprising the anion of the salt and the proton from the proton source material.

The sulfonium, selenonium and arsonium salts of this invention preferably comprise a chromophore which has a releasable, positive hydrogen ion. Upon exposure to visible radiation, an intramolecular rearrangement occurs which results in the formation of a Bronsted acid comprising the anion of the salt and the removable positive hydrogen ion. However, sulfonium, selenonium and arsonium salts can comprise a chromophore which does not contain a removable, positive hydrogen ion. Such salts are advantageously used in combination with a protonating agent and form, upon exposure to visible radiation, a Bronsted acid comprising the anion of the salt and the proton from the proton source material. The Bronsted acid is formed by an intermolecular reaction between the salt and the protonating material.

A particularly preferred class of onium salts is represented by the following formula:

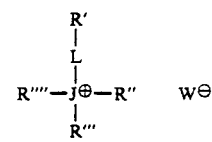

wherein:

R' represents an electron donating chromophore which absorbs visible radiation and which exhibits a higher energy occupied molecular orbital than at least one of R'', R''' and R'''', such as a coumarin group, preferably a hydroxy, methoxy or carboxy substituted coumarin group; a bifluorenylidene group, an anthracene group; a naphthacene group or a carbocyanine group, which groups can be further substituted with a group, such as methoxy, methyl, chloro, phenoxy, and thiomethyl to extend absorption of the chromophore to longer wavelength radiation or to fine tune the electronic absorption behavior of R';

L represents a linking group which essentially prevents $\pi$ resonance between R' and the remainder of the compound, and is preferably an optionally substituted alkylene linkage, advantageously containing from 1 to 18 carbon atoms, such as methylene, ethylene, propylene, butylene etc.; an ester linkage; an amide linkage, an arylene linkage such as a phenylene linkage; a sulfonate ester linkage, or, a sulfonamide linkage;

R" represents the same substituent as R' or R''', or an optionally substituted aryl group such as a phenyl group or a naphthyl group, or an optionally substituted alkyl group, advantageously having from 1 to 18 carbon atoms;

R''' represents an electron withdrawing alkyl, aryl or heterocyclic group, such as optionally substituted alkyl groups having from 1 to 18, and most preferably 1 to 4 carbon atoms; optionally substituent aryl groups have from 6 to 10 carbon atoms, and most preferably a phenyl group; and optionally substituent heterocyclic groups having from 1 to 4 rings and containing from 1 to 3 hetero atoms, such as N, S, O, Se or Te; preferably the R''' group contains an electron withdrawing group, such as halogen, preferably F, Cl or Br; CN, $NO_2$, $-SO_2-$, $CF_3$ and the like;

J represents an S, Se, As, N or P atom;

when J represents As, N or P, R'''' represents the same substituent as R', R" or R'''; and, when J represents an S or Se atom, R'''' represents either O or an electron pair; and, $W^\ominus$ represents an anion capable of forming a Bronsted acid preferably having a pKa of less than 7, such as $BF_4^-$, $ClO_4^-$, $AsF_6^-$, $PF_6^-$, $CH_3SO_3^-$, $CF_3SO_3^-$, $FeCl_4^-$, $BiCl_4^{-2}$, $SnCl_6^{-3}$, $AlF_6^{-3}$, $GaCl_4^-$, $TiF_6^-$, $ZrF_6^-$, $SbF_6^-$, or p-toluenesulfonate, said salt being capable, upon exposure to visible radiation of a wavelength absorbed by said chromophore, of forming a Bronsted acid. It will be noted that the salts of the invention can contain two electron donating chromophore groups, or two electron withdrawing groups.

Some highly preferred compounds are those in which, referring to the above formula:

R' represents one of the following chromophores:

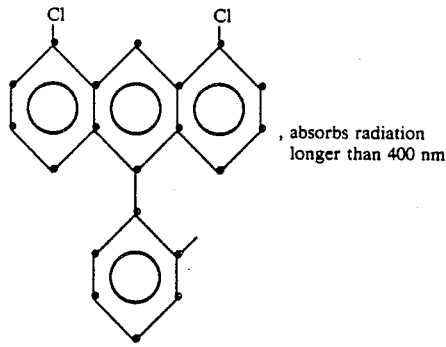, absorbs radiation longer than 400 nm

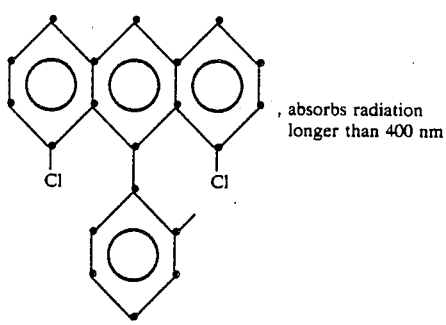, absorbs radiation longer than 400 nm

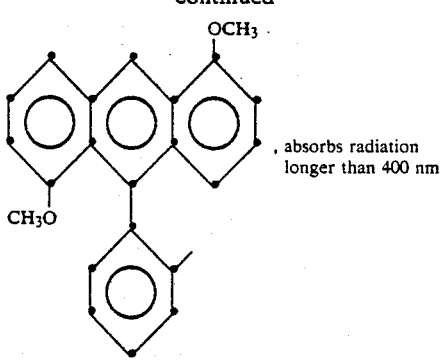, absorbs radiation longer than 400 nm

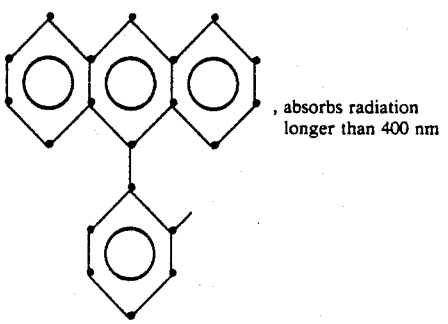, absorbs radiation longer than 400 nm

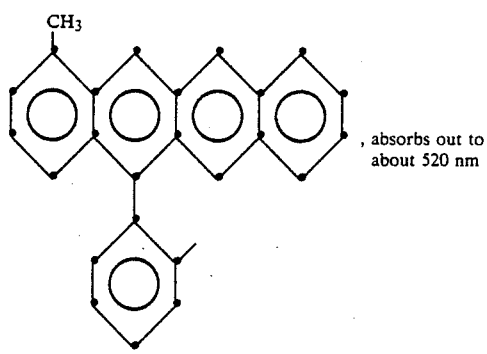, absorbs out to about 520 nm

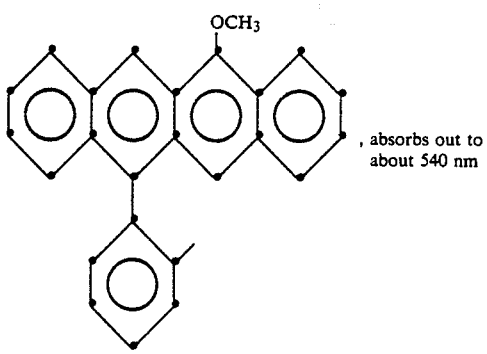, absorbs out to about 540 nm

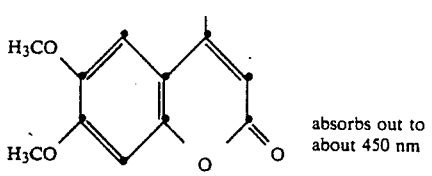 absorbs out to about 450 nm

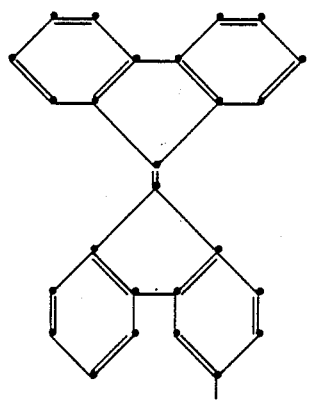
absorbs out to about 500 nm
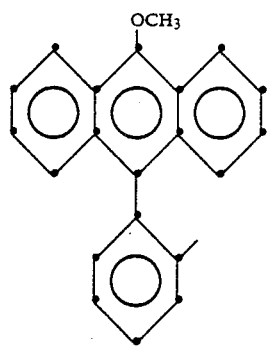
absorbs radiation longer than 400 nm
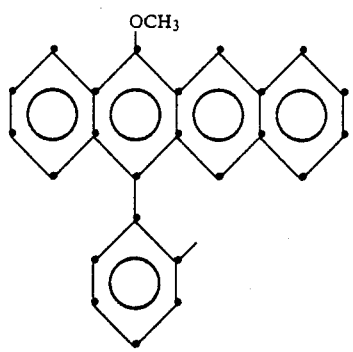
absorbs out to about 540 nm
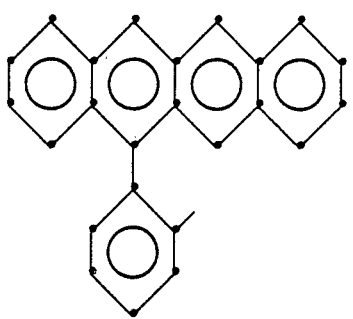
absorbs out to about 520 nm
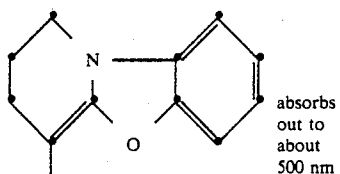
absorbs out to about 500 nm
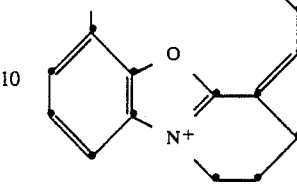
absorbs out to about 650 nm
L represents one of the following linkages:
$-(CH_2)_n-$, $-(CH_2-O)_n-$
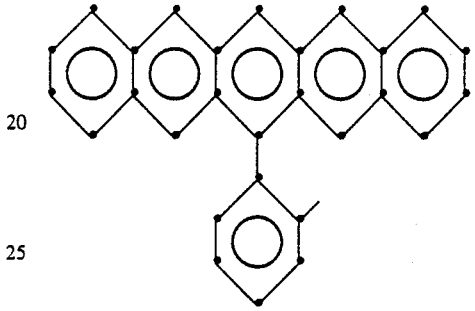
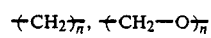
—CO$_2$—
—CONH—
wherein n represents 1 to 12;
J, R″, R‴ and R⁗, taken together, represent one of the following groups:
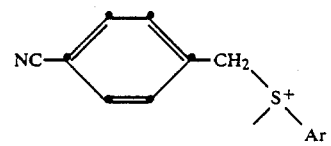
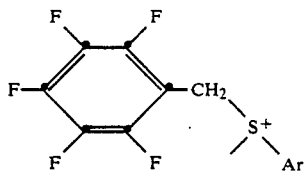

-continued

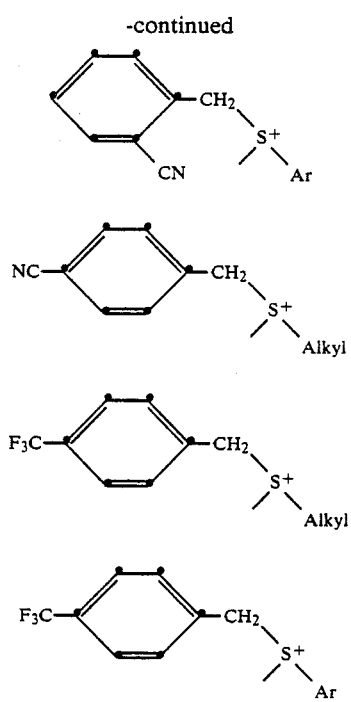

wherein Ar represents an optionally substituent aryl group, such as phenyl or naphthyl and alkyl represents an alkyl group such as methyl, ethyl, n-propyl or i-butyl; and W represents $BF_4$, $ClO_4$, $AsF_6$, $PF_6$, $CF_3SO_3$, $CH_3SO_3$, $SnCl_4$, $FeCl_4$, $BiCl_4$ and $SbF_6$.

Other highly useful compounds of this include compounds in which, referring to the above formula:

$R^1$ represents one of the following chromophores:

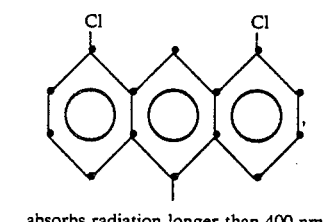

absorbs radiation longer than 400 nm

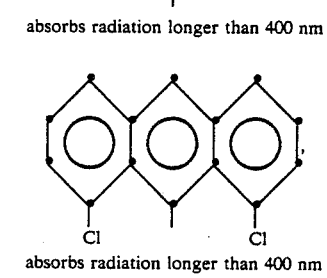

absorbs radiation longer than 400 nm

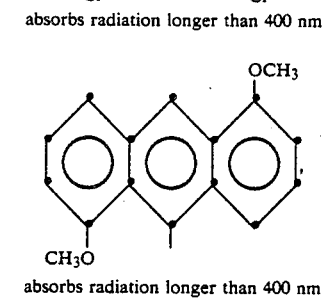

absorbs radiation longer than 400 nm

-continued

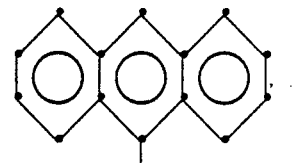

absorbs radiation longer than 400 nm

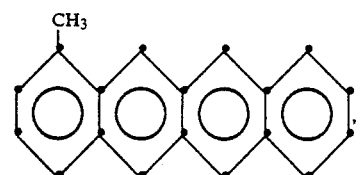

absorbs out to about 520 nm

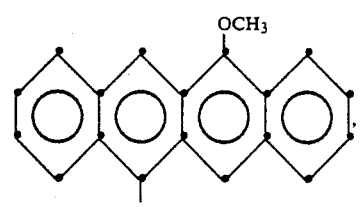

absorbs out to about 540 nm

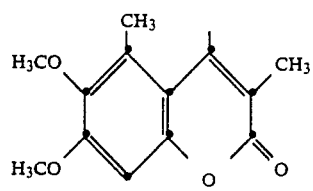

absorbs out to about 450 nm

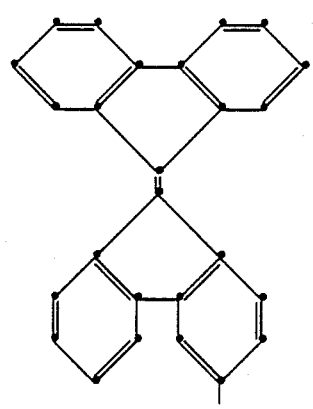

absorbs out to about 500 nm

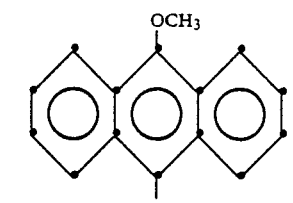

absorbs radiation longer than 400 nm

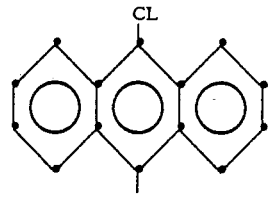

absorbs radiation longer than 400 nm

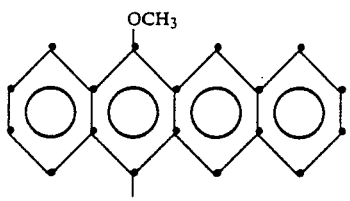

absorbs out to about 540 nm

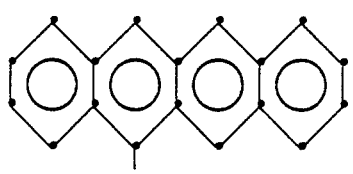

absorbs out to about 520 nm

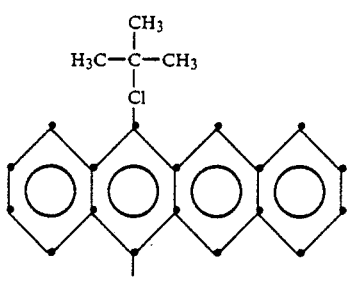

absorbs out to about 540 nm

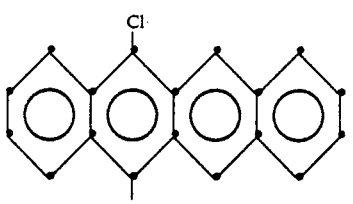

absorbs out to about 520 nm

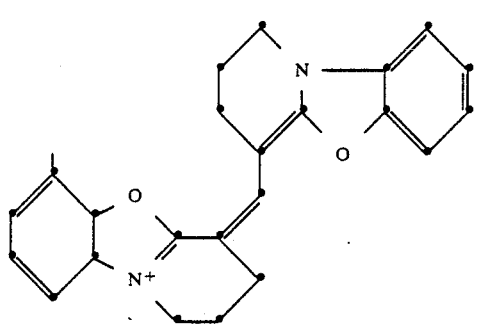

absorbs out to about 500 nm

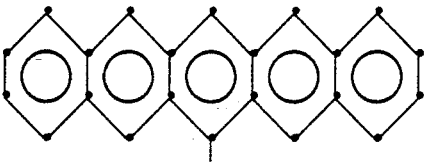

absorbs out to about 650 nm

L represents orthophenylene,

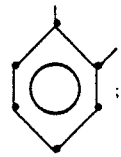

and J, R", R'" and R"", taken together, represent one of the following groups:

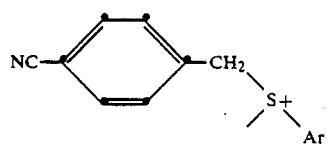

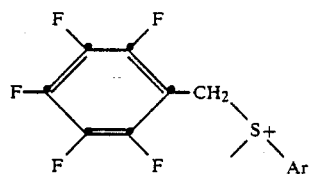

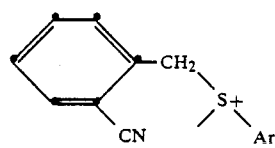

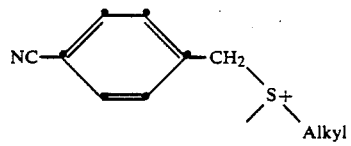

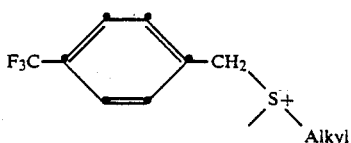

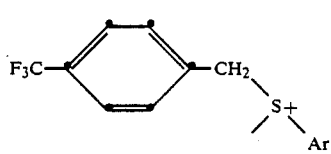

wherein Ar represents an optionally substituent aryl group, such as phenyl or naphthyl and alkyl represents an alkyl group such as methyl, ethyl, n-propyl or i-butyl; and W represents $BF_4$, $ClO_4$, $AsF_6$, $PF_6$, $CF_3SO_3$, $CH_3SO_3$, $SnCl_4$, $FeCl_4$, $BiCl_4$ and $SbF_6$.

The onium salts of this invention can be used in any application where it is desirable to release a Bronsted acid. The subject salts are especially useful in compositions which are curable by a Bronsted acid. Such compositions, also called cationically curable compounds, include cyclic formals and acetals, vinyl ethers, cyclic ethers, lactones, polysiloxanes, ureaformaldehyde resins, melamine-formaldehyde resins, and epoxides. A more comprehensive list is detailed in *Cationic Polymerization of Olefins: A Critical Inventory* J. P. Kennedy, Wiley Interscience Pub. 1975. Epoxy resins are particularly preferred.

The useful epoxy resins preferably contain a plurality of epoxy groups and may be based on the reaction product of Bisphenol A (i.e. 2,2-bis(4-hydroxyphenyl)propane) and epichlorohydrin, e.g. the resins sold under the registered Trademark Araldite by Ciba-Geigy Ltd., or are the reaction product of epichlorohydrin with a phenol-formaldehyde resin of relatively low molecular weight, e.g. epoxy-Novolaks (available, for example from Dow), or other modified epoxy resins as disclosed in *UV Curing: Science and Technology* (cited above). Still other useful epoxy resins and ether-containing materials polymerizable to a higher molecular weight are listed in Berggren et al U.S. Pat. No. 4,291,114 (1981) col. 4 line 37 through col. 6 line 23 and the silicone curable compositions disclosed by Eckberg U.S. Pat. No. 4,547,431 (1985) col. 3 line 29 through col. 4 line 17.

The onium salts of the invention can comprise from 0.1 to 30, and preferably from 1 to 25 percent by weight of the curable composition.

The onium salts of the invention can be used to provide protective coatings by imagewise or non-imagewise polymerization of monomers, e.g., the epoxide or ether containing monomers referred to above. The present onium salts can be used advantageously to provide overcoats for optical recording elements, such as those described by Thomas et al U.S. Pat. No. 4,380,769 issued Apr. 19, 1983. Such recording elements have on a support, in order, a smoothing layer, a reflection layer, a heat-deformable optical recording layer and a protective overcoat layer.

The onium salts of this invention are useful in making printing plates. For example, the onium salts of this invention and a material which can be chemically modified by a Bronsted acid can be solvent coated as a film onto an aluminum substrate. After the film has dried, it can be exposed to light absorbed by the chromophore of the onium salt, thus releasing a Bronsted acid. The film can be developed to produce a relief image by heating to vaporize chemical fragments from the exposed areas. The relief image can be inked and the resulting plate can be used as a printing plate. The relief image should be capable of being inked and capable of transferring the ink to a substrate, such as paper.

The onium salts of the invention can also be used in photoelectrographic elements which have a conductive layer in contact with an acid generating layer which contains an onium salt of the invention (the acid generating layer being free of photopolymerizable monomer), as described in Molaire et al U.S. patent application Ser. No. 856,543 filed Apr. 28, 1986. Such elements can be imagewise exposed, the acid photogenerating layer can be electrostatically charged, and the resultant electrostatic image can be developed with charged toning particles. Also, the onium salts of the invention can be used in the electrophotographic elements and process described in Scozzofava et al U.S. Pat. No. 4,485,161 issued Nov. 27, 1984.

The onium salts of the invention can also be used in the method of making color filter arrays which is described by Molaire et al U.S. patent application Ser. No. 871,748 filed Jun. 9, 1986. In that method, an electrophotographic element having a conductive layer in electrical contact with an acid photogenerating layer comprising an electrically insulating binder and being free of photopolymerizable materials, is imagewise exposed and electrostatically charged to form a latent image, and the latent image is developed with colored toner particles to form a single color array. Those steps can be repeated, with different colored toners to produce a multicolored filter array.

The onium salts of this invention are particularly useful as photoinitiators to produce imagewise release of chemical fragments in a polymer system for photoresist or printing plate applications.

The following examples are included for a further understanding of the invention.

The compounds of this invention can be prepared conveniently by the following reaction:

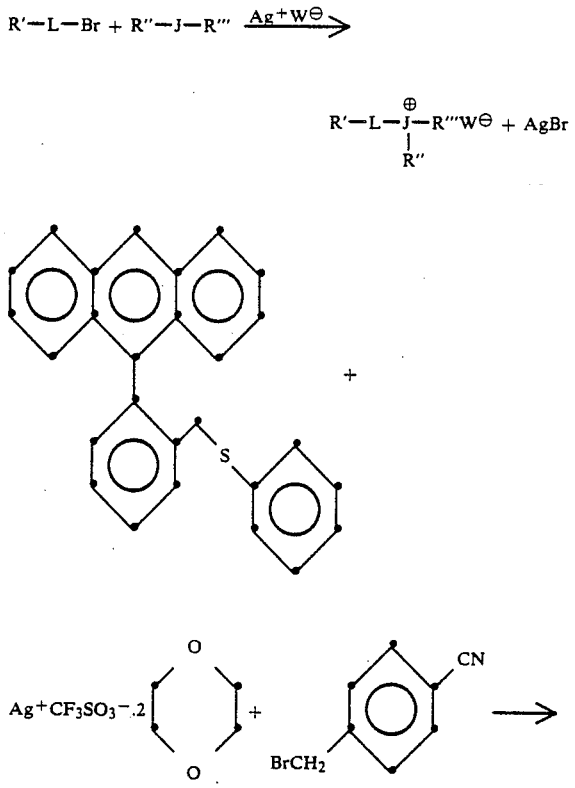

-continued

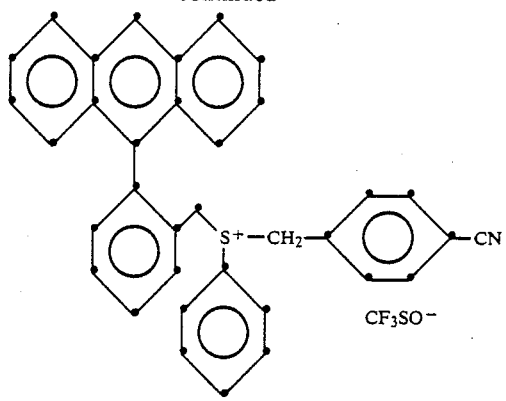

In a 100 ml round bottom flask was placed 2.00 gms. of the anthrylsulfide and 1.1 grams of p-cyanobenzyl bromide. To the solid mixture was added 30 ml of methylene chloride. A solution was formed. To the solution was added 2.4 grams of the appropriate silver salt. The reaction was allowed to stir overnight. An H$^1$NMR spectrum indicated about 80% conversion with no benzyl bromide present. The precipitated silver salts were filtered off. The methylene chloride solvent was removed by evaporation. To the semi-solid was added 5 mls of chloroform. The chloroform solution was dropped into 300 mls of carbon tetrachloride, the product oiled out. The carbon tetrachloride was decanted off and the product dissolved in acetonitrile. The acetonitrile solution was dropped into diethyl ether (100 ml). The product as off white solid was collected by filtration; the yield was 2.55 gms. The crude was recrystalized from CH$_3$CN/ether MP-127°-130° C. (dec).

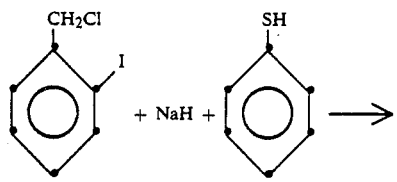

In a 250 ml 3 neck round bottom flask was placed 26 grams of sodium hydride. The hydride was washed with cyclohexane and then suspended in 100 mls of anhydrous THF (tetrahydrofuran). Then a solution of 4.4 grams of the thiophenol in 50 mls of THF was added dropwise over ½ hour, and allowed to stir for an additional ½ hour. Then a solution of 2-iodobenzylchloride 10 grams in 50 mls of THF was added. After 30 minutes the reaction was quenched with 10 mls of 10% HCl. Then ~200 mls of diethyl ether was added. The ether layer was extracted with dilute NaOH, and then with water. The ether layer was dried over MgSO$_4$ and flash evaporated to yield 12.5 grams of crude material. The crude product was distilled under vacuum. The product had a boiling point of 145°-150° C. (0.5 mmHg).

5-H,H-12-oxonaphthacene

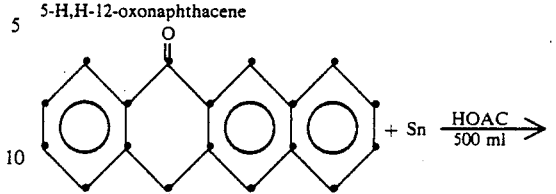

In a 1 l single neck round bottom was placed 20 grams of the 5,12-naphthacenequinone, 40 grams of Sn, and 500 mls of acetic acid. The mixture was refluxed for 1½ hours. Then 40 mls of concentrated HCl was added. The mixture was allowed to cool and the product was collected by suction filtration. Crude yield was 17 grams. Recrystallization from toluene provided 15 gm of purified product.

5-[2-thiomethylphenyl]naphthacene

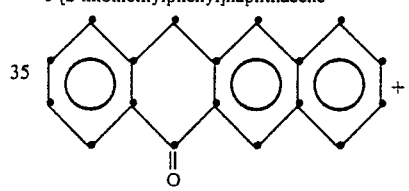

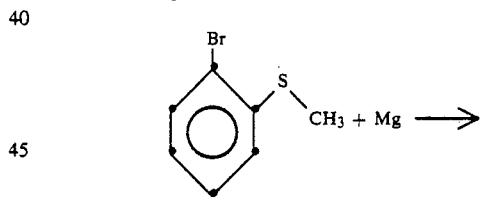

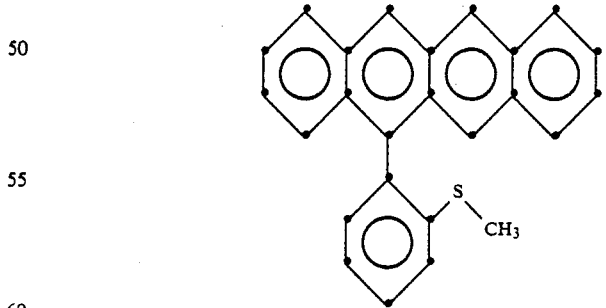

The Grignard reagent was formed by placing the aryl bromide, Mg, and 50 mls of anhydrous THF in a 100 ml round bottom flask and allowing the mixture to reflux for 4 hours. Then the 5-H,H-12-oxonaphthacene was added as a solid and the purple mixture was heated at reflux for 3 hours. The mixture was allowed to stir overnight at room temperature before adding 10 mls of concentrated HCl to the reaction mixture. The solution was heated at reflux for 15 minutes and cooled to room temperature. The reaction mixture was extracted with diethylether and the combined ether layers were extracted with 100 ml of 10% sodium carbonate, and then with water. The ether solution was dried with MgSO$_4$, filtered and flash evaporated. The solid was slurred in a small amount of EtOH and filtered. The crude product yield was 1.05 grams.

4-Cyanobenzyl-2-[5-naphthacenyl]phenylmethylsulfonium trifluoromethane sulfonate In a 15 ml round bottom flask was placed 0.1 gm (0.23 mmole) of 5-[2-thiomethylphenyl]naphthacene, 0.05 gm (0.25 mmol) of p-cyano- benzylbromide, and 5 ml of methylenechloride. Then 0.11 gm of silver trifluoromethane sulfonate di-dioxane was added and the reaction was allowed to stir for twenty four hours at room temperature. The methylene chloride was evaporated and 1 ml of acetonitrile was added. The insoluble silver salts were removed by filtration. The solution was then added to 150 ml of diethyl ether. The crude product crystallized and was collected by filtration. The product yield of 4-cyanobenzyl-2-[5-naphthacenyl]phenylmethyl sulfonium trifluoromethane sulfonate was 0.1 gm.

2-[5-naphthacenyl]benzylmethyl ether (A)

The Grignard reagent from 2-bromobenzylmethyl ether was prepared by adding magnesium to a solution of 2-bromobenzylmethyl ether in anhydrous THF and refluxing for 24 hours. Then the 5-oxo-12(H,H)-dihydronaphthacene was added as a solid. The solution was refluxed for 3 hours and cooled prior to the addition of concentrated HCl. The mixture was refluxed for an additional hour. Once the reaction mixture cooled to room temperature it was extracted with diethyl ether. The organic layer was then washed with a 10% bicarbonate solution, and finally with H$_2$O. The ether solution was dried with MgSO$_4$, filtered and flash evaporated to yield the crude product. The crude product was recrystallized from ethanol.

2-[5-napthacenyl]benzylbromide (B)

A solution of (A) in chloroform is treated with a steady stream of hydrogen bromide gas for 8 hours, and then allowed to stir for 16 hours. The reaction was washed with a bicarbonate solution, and with H$_2$O. The chloroform was dried with MgSO$_4$, and flash evaporated. The crude product was recrystallized from cyclohexane.

4-cyanobenzyl-2-[5-naphthacenyl]benzyldimethyl ammonium bromide (C)

A mixture of (B) and N,N-dimethyl-4-cyano benzylamine in acetonitrile was refluxed for 2 hours. The reaction mixture was then poured into diethyl ether, and the crude product was collected by filtration. The crude product was recrystallized from ethanol. The same reaction can be used to prepare the corresponding phosphonium and arsonium salts.

The following examples show the use of the salts of the invention to produce the imagewise release of chemical fragments in a polymer system for photoresist applications.

EXAMPLE 1

Imagewise Release of a Chemical Fragment 4-cyanobenzyl-2-[5-naphthacenyl]phenylmethyl sulfonium trifluoromethane sulfonate (I) (10% by weight) was dissolved in sufficient acetonitrile solvent along with polyvinyl (4-t-butylphenylcarbonate) as host polymer (90% by weight) to make a homogeneous solution. A film of the polymerphotoacid composition was cast onto a silicon wafer. The film was then irradiated in an imagewise fashion with an argon ion laser emitting at 488/515 nm. In the irradiated areas a Bronsted acid was produced which catalyzed the thermal transformation of the original polymer to polyvinylphenol after heating at 100° C. for 5–15 minutes. The regions containing the polyvinylphenol were then selectively removed with an aqueous base solution (10–50% hydroxide solution).

EXAMPLE 2

Imagewise Release of a Silane Chemical Fragment 4-cyanobenzyl-2-[5-naphthacenyl]phenyl sulfonium trifluoromethane sulfonate (I) (10% by weight) was dissolved in sufficient dichloromethane along with a polymer containing pendant allyl-t-butyldimethyl silyl groups (90% by weight) to make a homogeneous solution. A film of the polymer- photoacid composition was cast onto a silicon wafer. The film was then irradiated in an imagewise fashion using an argon ion laser emitting at 488/515 nm. In the irradiated area a Bronsted acid was produced which catalyzed the thermal transformation to the vinyl polymer without the pendant silane functionality. Exposure of the irradiated and heated film to an oxygen plasma selectively removed the irradiated areas by a completely dry process.

EXAMPLE 3

Imagewise Release of a Chemical Fragment 4-cyanobenzyl-2-[5-naphthacenyl]phenylmethyl sulfonium trifluoromethane sulfonate (I) (10% by weight) was dissolved in sufficient acetonitrile solvent along with polyvinyl (4-t-butylphenylcarbonate) as host polymer (90% by weight) to make a homogeneous solution. A film of the polymer photoacid composition was cast onto a silicon wafer. The film was then irradiated in an imagewise fashion with an argon ion laser emitting at 488/515 nm. In the irradiated areas a Bronsted acid was produced which catalyzed the thermal transformation of the original polymer to polyvinylphenol after heating at 100° C. for 5–15 minutes. The regions containing the polyvinylphenol were then selectively removed with an aqueous base solution (10–50% hydroxide solution).

EXAMPLE 4

Imagewise Release of a Silane Chemical Fragment 4-cyanobenzyl-2-[5-naphthacenyl]phenylmethyl sulfonium trifluoromethane sulfonate (I) (10% by weight) with a polymer containing pendant allyl-t-butyl-dimethyl silyl groups (90% by weight) to make a homogeneous solution. A film of the polymer photoacid composition was cast onto a silicon wafer. The film was then irradiated in an imagewise fashion using an argon ion laser emitting at 488/515 nm. In the irradiated area a Bronsted acid was produced which catalyzed the thermal transformation to the vinyl polymer without the pendant silane functionality. Exposure of the irradiated and heated film to an oxygen plasma selectively removed the irradiated areas by a completely dry process.

Results similar to those described in the above examples can be obtained with other sulfonium and arsonium salts of the type described above. Also, by employing a protonating material such as water or an alcohol, similar results can be obtained with the phosphonium and ammonium salts described above, and with the sulfonium, selenonium and arsonium salts described above but in which the chromophore does not contain a removable, positive hydrogen ion.

The following examples illustrate polymer coatings by photoinduced cationic polymerization of epoxide monomers and prepolymers.

EXAMPLE 5

Phenyl-p-cyanobenzyl-4-[6,7-dimethoxycoumarin methyl] sulfonium trifluoromethanesulfonate (0.1 g) was dissolved in methylene chloride (10 ml) along with cyclohexene oxide (1.0) g and the mixture coated onto a glass substrate and irradiated with visible light from a 200 Watt Hg-Xe lamp positioned 4″ from the substrate. The solution polymerized after exposure to visible radiation for 1 minute and heating at 50° C. for 30 minutes. Polymerization was initiated by the Bronsted acid released when the sulfonium salt was irradiated.

EXAMPLE 6

Phenyl-p-cyanobenzyl-9-[2-phenylmethyl] anthryl sulfonium trifluoromethane sulfonate (0.2 g) was dissolved in methylene chloride (2 ml) along with an epoxy prepolymer (1.0). A film of the prepolymersulfonium sensitizer composition was formed on a glass substrate by spin coating. The thin film (~5 micrometers) was irradiated for 2 minutes with a 200 Watt Hg-Xe lamp as previously described. The polymer film became tough and cross-linked after heating at 50° C. for 30 minutes. Cross-linking was initiated by the Bronsted acid released when the sulfonium salt was irradiated.

EXAMPLE 7

Phenyl-p-cyanobenzyl-4-[bifluorenylidene methyl] sulfonium hexafluorophosphate (0.2) was dissolved in methylene chloride (2 ml) along with an epoxy prepolymer (1.0 g). A film of the prepolymersulfonium sensitizer composition was formed on a glass substrate by spin coating. The thin film (~5 micrometers) was irradiated for 2 minutes with a 200 Watt Hg-Xe lamp as previously described. The polymer film became tough and cross-linked after heating at 50° C. for 30 minutes. Cross-linking was initiated by the Bronsted acid released when the sulfonium salt was irradiated.

EXAMPLE 8

Methyl-p-cyanobenzyl-9-[2-phenylmethyl] anthryl sulfonium trifluoromethane sulfonate (0.2 g) was dissolved in methylene chloride (2 ml) along with an epoxy prepolymer (1.0 g). A film of the prepolymersulfonium sensitizer composition was formed on a glass substrate by spin coating. The thin film (~5 micrometers) was irradiated for 2 minutes with a 200 Watt Hg-Xe lamp as previously described. The polymer film became tough and cross-linked after heating at 50° C. for 30 minutes. Cross-linking was initiated by the Bronsted acid released when the sulfonium salt was irradiated.

EXAMPLE 9

Methyl-p-cyanobenzyl-4-[bifluorenylidene-2-phenyl] sulfonium hexafluorophosphate (0.2) was dissolved in methylene chloride (2 ml) along with an epoxy prepolymer (1.0 g). A film of the prepolymersulfonium sensitizer composition was formed on a glass substrate by spin coating. The thin film (~5 micrometers) was irradiated for 2 minutes with a 200 Watt Hg-Xe lamp as previously described. The polymer film became tough and cross-linked after heating at 50° C. for 30 minutes. Cross-linking was initiated by the Bronsted acid released when the sulfonium salt was irradiated.

The following examples illustrate imagewise dye absorption changes as a result of dye protonation.

EXAMPLE 10

Phenyl-p-cyanobenzyl-4-[6,7-dimethoxycoumarin methyl] sulfonium trifluoromethanesulfonate (1.0 g) was dissolved in methylene chloride (5 ml) along with polystyrene, MW=100,000, (1.0 g) and propyl red indicator (0.001 g). A film of the above composition was formed on a 1″ round disc (⅛′ thick) by spin coating. The polymer film was then exposed to visible light from a Hg-Xe lamp positioned 4″ from the substrate for 3 minutes. The initially yellow film turned red after the irradiation was complete as a result of the Bronsted acid released from the sulfonium salt and protonation of the propyl red indicator.

EXAMPLE 11

Methyl-p-cyanobenzyl-4-[6,7-dimethoxycoumarin-2-phenyl] sulfonium trifluoromethanesulfonate (1.0 g) was dissolved in methylene chloride (5 ml) along with polystyrene, MW=100,000, (1.0 g) and propyl red indicator (0.001 g). A film of the above composition was formed on a 1″ round disc (⅛′ thick) by spin coating. The polymer film was then exposed to visible light from a Hg-Xe lamp positioned 4″ from the substrate for 3 minutes. The initially yellow film turned red after the irradiation was complete as a result of the Bronsted acid released from the sulfonium salt and protonation of the propyl red indicator.

The following examples illustrate imagewise conductive films for electrophotographic copying, circuit board fabrication, and fabrication of color filter arrays.

EXAMPLE 12

Phenyl-p-cyanobenzyl-4-[6,7-dimethoxycoumarin methyl] sulfonium hexafluorophosphate (0.1 g) was dissolved in methylene chloride (5 ml) along with polystyrene, MW=100,000, (1.0 g). A film of the above composition was cast onto a conductive substrate of either aluminum or nesa (InSnO) glass by spin coating. The solvent was allowed to evaporate in a vaccuum oven with heating (25°–50° C. for 30 minutes). The polymer film was then exposed to visible light from a Hg-Xe lamp through a mask for 1 minute. The film was then charged with either a positive or negative corona while the conductive layer was held to ground. The ion-charge discharges more rapidly in the irradiated areas due to the presence of a Bronsted acid to produce a latent charged image which can be visualized by the conventional toning procedure. Transfer of the toned image to paper converts it to a permanent state. Additional copies of the charged image can be made by repeating the charging, toning, and transfer process without repeating the exposure step.

EXAMPLE 13

Methyl-p-cyanobenzyl-4-[6,7-dimethoxycoumarin-2-phenyl] sulfonium hexafluorophosphate (0.1 g) was dissolved in methylene chloride (5 ml) along with polystyrene, MW=100,000, (1.0 g). A film of the above composition was cast onto a conductive substrate of either aluminum or nesa (InSnO) glass by spin coating. The solvent was allowed to evaporate in a vacuum oven with heating (25°–50° C. for 30 minutes). The polymer film was then exposed to visible light from a Hg-Xe lamp through a mask for 1 minute. The film was then charged with either a positive or negative corona while the conductive layer was held to ground. The ion-charge discharges more rapidly in the irradiated areas due to the presence of a Bronsted acid to produce a latent image which can be visualized by the conventional toning procedure. Transfer of the toned image to paper converts it to a permanent state. Additional copies of the charged image can be made by repeating the charging, toning, and transfer process without repeating the exposure step.

The following examples illustrate the use of Bronsted photoacids for the production of printing plate masters.

EXAMPLE 14

Printing Plate Masters 4-cyanobenzyl-2-[5-naphthacenyl]benzyl phenyl sulfonium trifluoromethanesulfonate (I) (10% by weight) was dissolved in sufficient acetonitrile solvent along with polyvinyl-(4-t-butylphenylcarbonate) as host polymer (90% by weight) to make a homogeneous solution. A film (~5 microns) of the polymerphotoacid composite was cast onto a flexible rectangular aluminum substrate 10"×12" in dimensions. After drying at 50 degrees for 10 minutes, the film was exposed in an imagewise fashion with an argon-ion laser. Development to produce a relief image in the exposed areas was achieved by heating the film to 100 degrees for 5 minutes. The aluminum substrate was then wrapped around a drum with the relief image exposed. The raised pattern could be selectively inked and the inked image transferred to a substrate such as paper. This process could be repeated many times.

EXAMPLE 15

Printing Plate Masters 4-cyanobenzyl-2-[5-naphthacenyl]phenylmethyl sulfonium trifluoromethanesulfonate (I) (10% by weight) was dissolved in sufficient acetonitrile solvent along with polyvinyl-(4-t-butylphenylcarbonate) as host polymer (90% by weight) to make a homogeneous solution. A film (~5 microns) of the polymerphotoacid composite was cast onto a flexible rectangular aluminum substrate 10"×12" in dimensions. After drying at 50 degrees for 10 minutes, the film was exposed in an imagewise fashion with an argon-ion laser. Development to produce a relief image in the exposed areas was achieved by heating the film to 100 degrees for 5 minutes. The aluminum substrate was then wrapped around a drum with the relief image exposed. The raised pattern could be selectively inked and the inked image transferred to a substrate such as paper. This process could be repeated many times.

EXAMPLE 16

Printed Circuit Board Fabrication 4-cyanobenzyl-2-[5-naphthacenyl]phenyl methylsulfonium trifluoromethanesulfonate (0.1 gm) and poly(4-t-butylphenylcarbonate) (1.9 gm) were dissolved in 5 ml of dichloromethane. A 1 mil film of the above composition was cast onto a copper substrate and allowed to dry for 15 minutes at 60° C. The film was exposed for two minutes in an imagewise fashion through a test target with a 5 watt argon-ion laser. The film was heat treated at 100° C. for 1 minute before development to remove the exposed regions with a 20% $Na_2CO_3$ solution. The exposed copper was etched with a nitric acid solution in the presence of molecular oxygen to produce a copper pattern for a printed circuit board.

This invention has been described in detail with particular reference to preferred embodiments thereof, but it will be understood that variations and modifications can be affected within the spirit and scope of the invention.

What is claimed is:

1. A composition of matter comprising a material curable by a Bronsted acid, and a sulfonium, selenonium, arsonium, ammonium or phosphonium salt comprising:

a chromophore which absorbs visible radiation, said chromophore exhibiting a higher energy occupied molecular orbital than at least one other substituent attached to the S, Se, As, N or P atom of said salt;

an insulating group which links said chromophore to the S, Se, As, N or P atom of said salt, said insulating group essentially preventing $\pi$ resonance between said chromophore and the other substituents in said salt;

at least one substituent comprising an electron withdrawing group and exhibiting a lower unoccupied molecular orbital than said chromophore; and, an anion;

said salt being capable, upon exposure to visible radiation, of forming a Bronsted acid.

2. A composition of matter as defined in claim 1 wherein said salt is a sulfonium or arsonium salt which comprises:

a chromophore which absorbs visible radiation, said chromophore (1) having a removable positive hydrogen ion and (2) exhibiting a higher energy occupied molecular orbital than at least one other substituent attached to the S or As atom of said salt;

an insulating group which links said chromophore to the S or As atom of said salt, said insulating group essentially preventing $\pi$ resonance between said chromophore and the other substituents in said salt;

at least one substituent comprising an electron withdrawing group and exhibiting a lower unoccupied molecular orbital than said chromophore; and, an anion;

said salt being capable, upon exposure to visible radiation, of forming, by an intramolecular rearrangement, a Bronsted acid comprising the anion of said salt and said removable hydrogen ion.

3. A composition of matter as defined in claim 2 wherein said salt is a sulfonium salt which comprises:

a chromophore which absorbs visible radiation, said chromophore (1) having a removable positive hydrogen ion, and (2) exhibiting a higher energy occupied molecular orbital than at least one other substituent directly attached to the sulfur atom of said salt;

an insulating group which links said chromophore to the sulfur atom of said salt, said insulating group essentially preventing π resonance between said chromophore and the other substituents in said salt;

at least one substituent comprising an electron withdrawing group and exhibiting a lower unoccupied molecular orbital than said chromophore; and, an anion;

said salt being capable, upon exposure to visible radiation, of forming, by an intramolecular rearrangement, a Bronsted acid comprising the anion of said salt and said removable hydrogen ion.

4. A composition of matter as defined in claim 1 wherein said salt has the following formula:

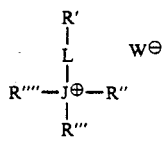

wherein:

R' represents an electron donating chromophore group which absorbs visible radiation, and which exhibits a higher energy occupied molecular orbital than at least one of R'', R''' and R'''';

R'' represents the same substituent as R' or R''', an optionally substituted aryl group or an optionally substituted alkyl group having from 1 to 18 carbon atoms;

L represents a linking group which essentially prevents π resonance between R' and the remainder of the compound;

R''' represents an electron withdrawing alkyl, aryl or heterocyclic group;

J represents an S, Se, As, N or P atom; and when J represent As, N or P, R'''' represents the same substituent as R', R'' or R''' and, when J represents a S or Se atom, R'''' represents O or an electron pair; and, W$^\ominus$ represents an anion capable of forming a Bronsted acid having a pKa of less than 7, said compound being capable, upon exposure to visible radiation of a wavelength absorbed by said chromophore, of forming a Bronsted acid.

5. A composition of matter as defined in claim 1 wherein said salt has the following formula:

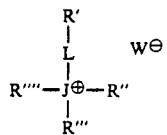

wherein:

R' represents an electron donating chromophore group which absorbs visible radiation, has a removable positive hydrogen ion, and exhibits a higher energy occupied molecular orbital than at least one of R'', R''' and R'''';

R'' represents the same substituent as R' or R''', an optionally substituted aryl group or an optionally substituted alkyl group;

L represents a linking group which essentially prevents π resonance between R' and the remainder of the compound;

R''' represents an electron withdrawing alkyl, aryl or heterocyclic group;

J represents a sulfur, selenium or arsenic atom;

when J represents As, R'''' represents the same substituent as R', R'' or R''' and when J represents a sulfur or selnium atom, R'''' represents O or an electron pair; and, W$^\ominus$ represents an anion capable of forming a Bronsted acid having a pKa of less than 7;

said compound being capable, upon exposure to visible radiation of a wavelength absorbed by said chromophore, of forming, by intramolecular rearrangement, a Bronsted acid comprising W and said removable positive hydrogen of R'.

6. A composition of matter as defined in claim 1 wherein said salt has the following formula:

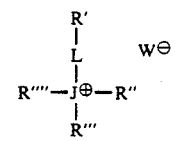

wherein:

R' represents an electron donating chromophore group which absorbs visible radiation, has a removable positive hydrogen ion, and exhibits a higher energy occupied molecular orbital than at least one of R'', R''' and R'''';

R'' represents the same substituent as R' or R''', an optionally substituted aryl group or an optionally substituted alkyl group;

L represents a linking group which essentially prevents π resonance between R' and the remainder of the compound;

R''' represents an electron withdrawing alkyl, aryl or heterocyclic group;

J represents a sulfur atom;

R'''' represents O or an electron pair; and,

W$^\ominus$ represents an anion capable of forming a Bronsted acid having a pKa of less than 7;

said compound being capable, upon exposure to visible radiation of a wavelength absorbed by said chromophore, of forming, by intramolecular rearrangement, a Bronsted acid comprising W$^\ominus$ and said removable positive hydrogen of R'.

7. A composition of matter comprising a material curable by a Bronsted acid and a compound having the formula:

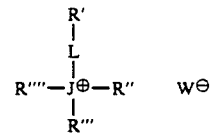

wherein:

R' represents one of the following chromophores:

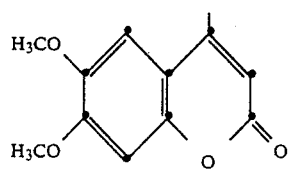
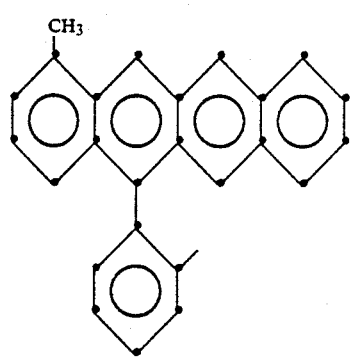
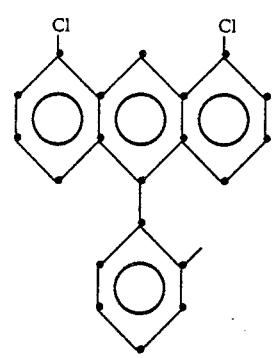
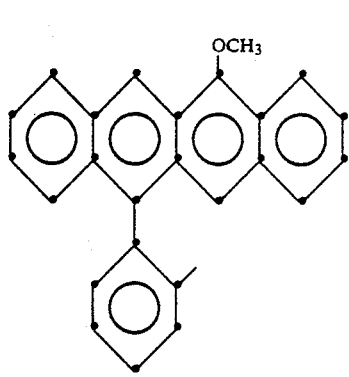
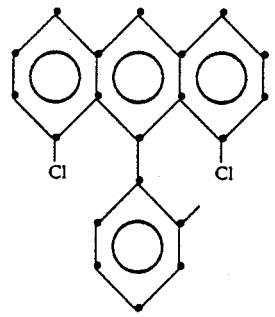
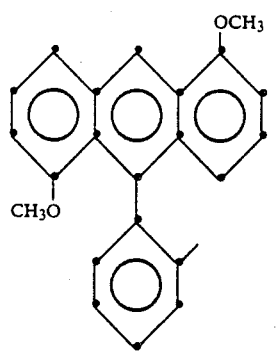
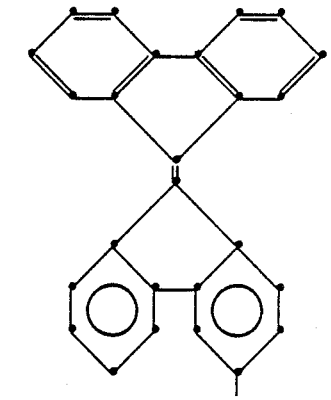
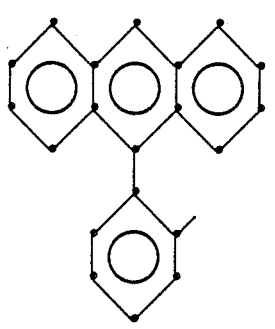
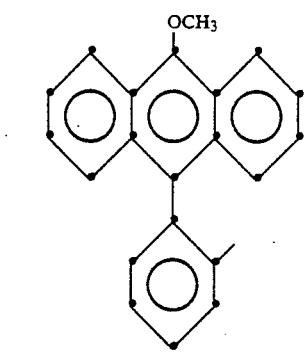

-continued

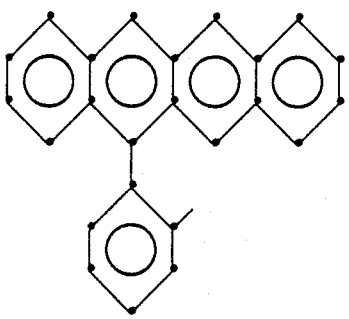

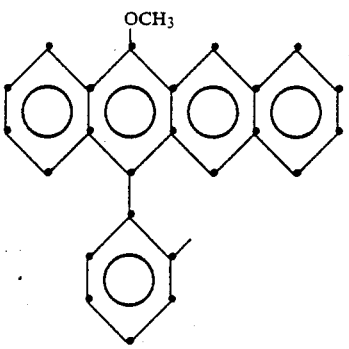

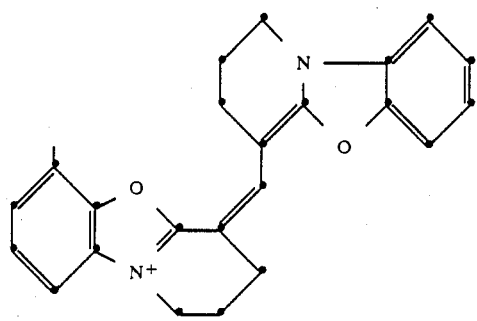

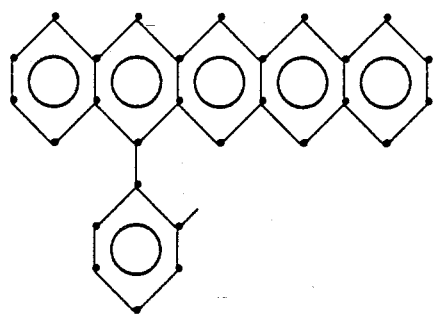

L represents one of the following linkages:

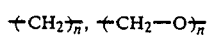

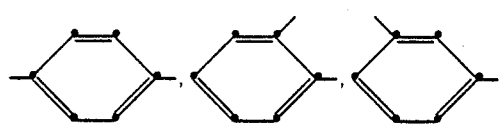

-continued

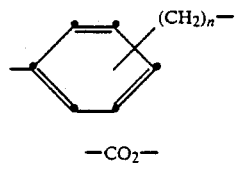

—CO$_2$—

—CONH— wherein n represents 1 to 12;

J, R″, R‴ and R⁗, taken together, represent one of the following groups:

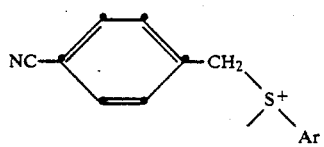

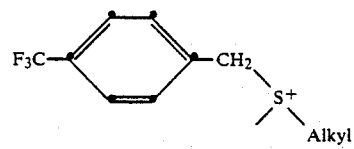

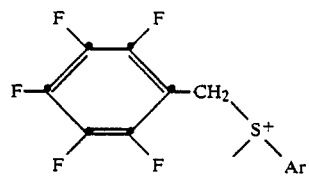

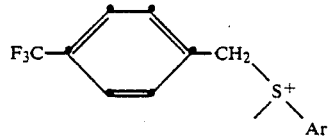

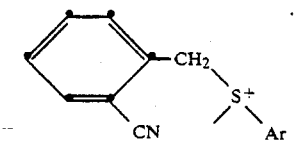

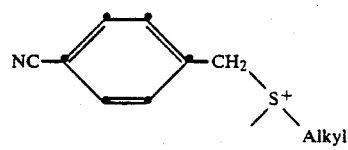

wherein Ar represents an optionally substituent aryl group; and

W represents BF$_4$, ClO$_4$, AsF$_6$, PF$_6$, CF$_3$SO$_3$, CH$_3$SO$_3$, SnCl$_4$, FeCl$_4$, BiCl$_4$ or SbF$_6$.

8. A method of curing which comprises exposing to visible radiation (1) a material curable by a Bronsted acid and (2) a sulfonium, selenonium, arsonium, ammonium or phosphonium salt comprising:

a chromophore which absorbs said visible radiation, said chromophore exhibiting a higher energy occupied molecular orbital than at least one other substituent attached to the S, Se, As, N or P atom of said salt;

an insulating group which links said chromophore to the S, Se, As, N or P atom of said salt, said insulating group essentially preventing π resonance between said chromophore and the other substituents in said salt;

at least one substituent comprising an electron withdrawing group and exhibiting a lower unoccupied molecular orbital than said chromophore; and, an anion;

said salt being capable, upon exposure to said visible radiation, of forming a Bronsted acid.

9. A method of curing as defined in claim 8 wherein said salt is a sulfonium or arsonium salt comprising:

a chromophore which absorbs said visible radiation, said chromophore (1) having a removable positive hydrogen ion and (2) exhibiting a higher energy occupied molecular orbital than at least one other substituent directly attached to the S or As atom of said salt;

an insulating group which links said chromophore to the S or As atom of said salt, said insulating group essentially preventing π resonance between said chromophore and the other substituents in said salt;

at least one substituent comprising an electron withdrawing group and exhibiting a lower unoccupied molecular orbital than said chromophore; and, an anion;

said salt being capable, upon exposure to said visible radiation, of forming, by an intramolecular rearrangement a Bronsted acid comprising the anion of said salt and said removable hydrogen ion.

10. A method of curing as defined in claim 8 wherein said salt is a sulfonium salt comprising:

material curable by a Bronsted acid and (2) a sulfonium salt comprising:

a chromophore which absorbs said visible radiation, said chromophore (1) having a removable positive hydrogen ion, and (2) exhibiting a higher energy occupied molecular orbital than at least one other substituent attached to the sulfur atom of said salt;

an insulating group which links said chromophore to the sulfur atom of said salt, said insulating group essentially preventing π resonance between said chromophore and the other substituents in said salt;

at least one substituent comprising an electron withdrawing group and exhibiting a lower unoccupied molecular orbital than said chromophore; and, an anion;

said salt being capable, upon exposure to said visible radiation, of forming, by an intramolecular rearrangement, a Bronsted acid comprising the anion of said salt and said removable hydrogen ion.

11. A method of curing as defined in claim 8 wherein said salt has the following formula:

wherein:

R' represents an electron donating chromophore group which absorbs said visible radiation, has a removable positive hydrogen ion, and exhibits a higher energy occupied molecular orbital than at least one of R", R''' and R'''';

R" represents the same substituent as R' or R''', an optionally substituted aryl group or an optionally substituted alkyl group;

L represents a linking group which essentially prevents π resonance between R' and the remainder of the compound;

R''' represents an electron withdrawing alkyl, aryl or heterocyclic group;

J represents a sulfur or arsonium atom;

when J represents As, R'''' represents the same substituent as R', R" or R''' and when J represents a sulfur atom, R'''' represents O or an electron pair; and, W$^\ominus$ represents an anion capable of forming a Bronsted acid having a pKa of less than 7;

said compound being capable, upon exposure to said visible radiation, of forming, by intramolecular rearrangement, a Bronsted acid comprising W and said removable positive hydrogen of R'.

12. A method of curing as defined in claim 8 wherein said salt has the following formula:

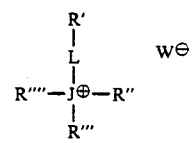

wherein:

R' represents an electron donating chromophore group which absorbs said visible radiation, has a removable positive hydrogen ion, and exhibits a higher energy occupied molecular orbital than at least one of R", R''' and R'''';

R" represents the same substituent as R' or R''', an optionally substituted aryl group or an optionally substituted alkyl group;

L represents a linking group which essentially prevents π resonance between R' and the remainder of the compound;

R''' represents an electron withdrawing alkyl, aryl or heterocyclic group;

J represents a sulfur atom;

R'''' represents O or an electron pair; and,

W$^\ominus$ represents an anion capable of forming a Bronsted acid having a pKa of less than 7;

said compound being capable, upon exposure to said visible radiation, of forming, by intramolecular rearrangement, a Bronsted acid comprising W$^\ominus$ and said removable positive hydrogen of R'.

13. A method of curing as defined in claim 8 wherein said salt has the following formula: material curable by a Bronsted acid and (2) a compound having the formula:

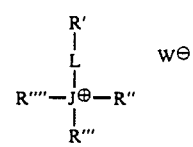

wherein:

R' represents one of the following chromophores:

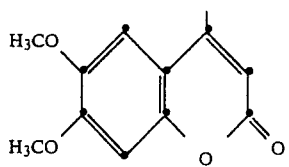
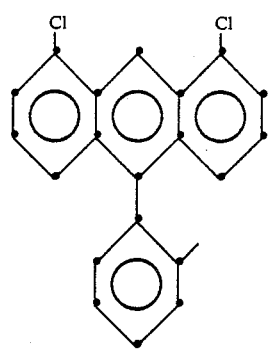
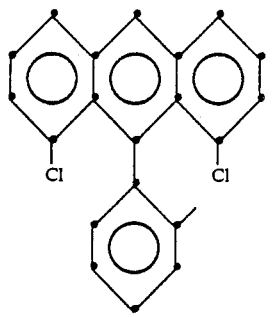
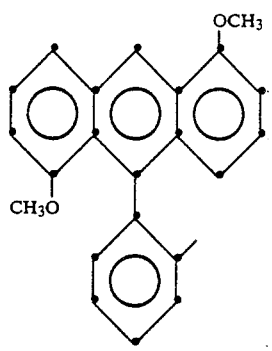
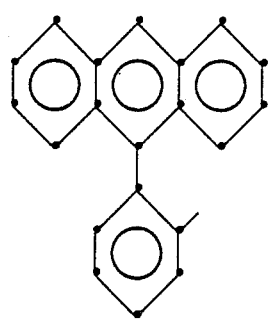
-continued
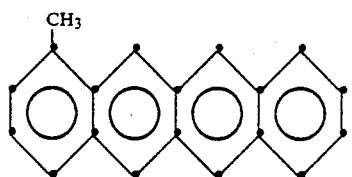
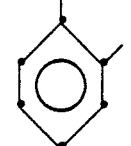
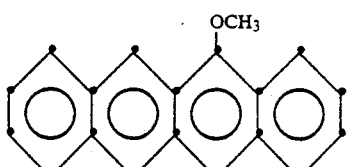
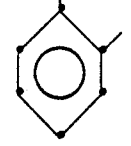
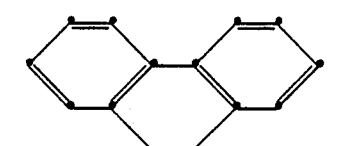
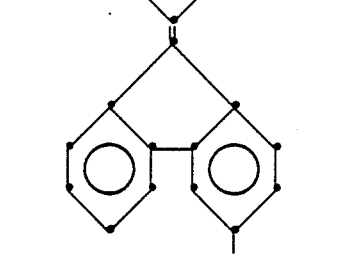
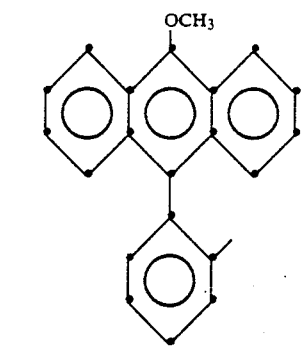

-continued

[structure: tetracene with phenyl substituent]

[structure: bis-indoline-type cyanine/merocyanine]

[structure: pentacene with phenyl substituent]

L represents one of the following linkages:

$+CH_2+_n$, $+CH_2-O+_n$

[three phenylene linker structures]

[phenylene-(CH$_2$)$_n$— linker]

—CO$_2$—

—CONH— wherein n represents 1 to 12;

J, R", R''' and R'''', taken together, represent one of the following groups:

[structure: NC-C$_6$H$_4$-CH$_2$-S$^+$(—)(Ar)]

[structure: F$_3$C-C$_6$H$_4$-CH$_2$-S$^+$(—)(Alkyl)]

[structure: pentafluorophenyl-CH$_2$-S$^+$(—)(Ar)]

[structure: F$_3$C-C$_6$H$_4$-CH$_2$-S$^+$(—)(Ar)]

[structure: 2-CN-C$_6$H$_4$-CH$_2$-S$^+$(—)(Ar)]

[structure: NC- and CN-disubstituted C$_6$H$_3$-CH$_2$-S$^+$(—)(Alkyl)]

wherein Ar represents an optionally substituent aryl group and alkyl represents an alkyl group from $C_1$ to $C_{10}$; and $W^\ominus$ represents $BF_4$, $ClO_4$, $AsF_6$, $PF_6$, $CF_3SO_3$, $CH_3SO_3$, $SnCl_4$, $FeCl_4$, $BiCl_4$ or $SbF_6$.

14. A method of curing which comprises exposing to visible radiation (1) a material curable by a Bronsted acid and (2) a compound having the formula:

$$R''''-J^\oplus-R'' \quad W^\ominus$$
with R' (via L) above J and R''' below J wherein:
R' represents an electron donating chromophore group which absorbs said visible radiation, and which exhibits a higher energy occupied molecular orbital than at least one of R", R''' and R'''';
R" represents the same substituent as R' or R''', an optionally substituted aryl group or an optionally substituted alkyl group having from 1 to 18 carbon atoms;
L represents a linking group which essentially prevents π resonance between R' and the remainder of the compound;

R''' represents an electron withdrawing alkyl, aryl or heterocyclic group;

J represents an S, Se, As, N or P atom; and when J represents As, N or P, R'''' represents the same substituent as R', R'' or R''' and, when J represents an S or Se atom, R'''' represents O or an electron pair; and, W⊖ represents an anion capable of forming a Bronsted acid having a pKa of less than 7, said compound being capable, upon exposure to visible said radiation, of forming a Bronsted acid.

15. A composition of matter comprising a material curable by a Bronsted acid and a salt having the following formula:

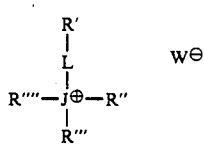

wherein:

R' represents an electron donating chromophore group which absorbs visible radiation, and which exhibits a higher energy occupied molecular orbital than at least one of R'', R''' and R'''';

R'' represents the same substitutent as R' or R''', an optionally substituted aryl group or an optionally substituted alkyl group having from 1 to 18 carbon atoms;

L represents orthophenylene;

R''' represents an electron withdrawing alkyl, aryl or heterocyclic group;

J represents an S, Se, As, N or P atom; and when J represent As, N or P, R'''' represents the same substituent as R', R'' or R''' and, when J represents a S or Se atom, R'''' represents O or an electron pair; and, W⊖ represents an anion capable of forming a Bronsted acid having a pKa of less than 7, said compound being capable, upon exposure to visible radiation of a wavelength absorbed by said chromophore, of forming a Bronsted acid.

16. A composition of matter as defined in claim 15 wherein said salt has the formula:

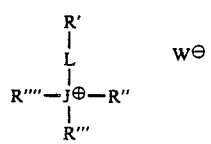

wherein:

R' represents one of the following chromophores:

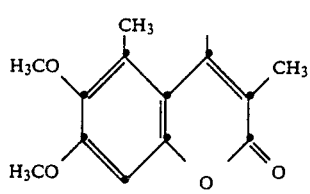

-continued

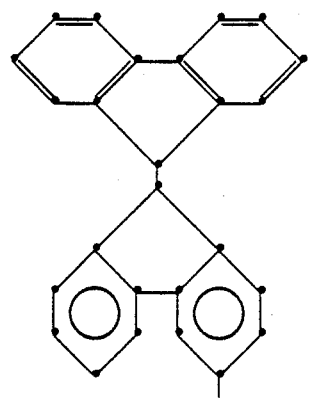

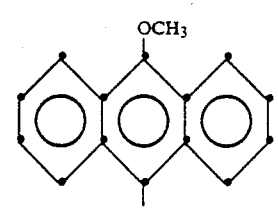

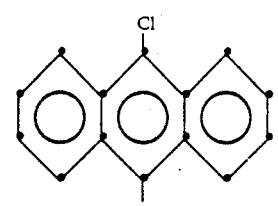

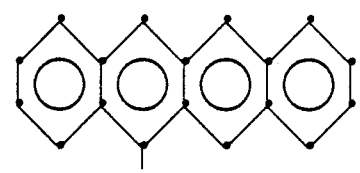

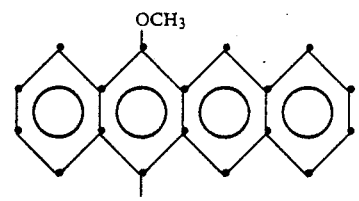

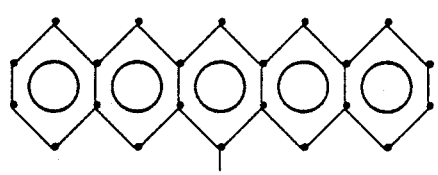

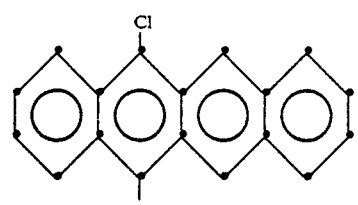

-continued

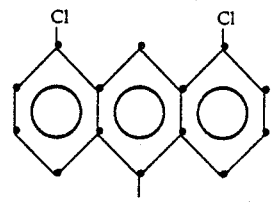,

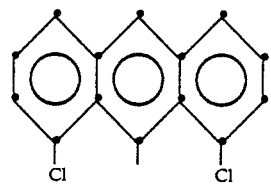,

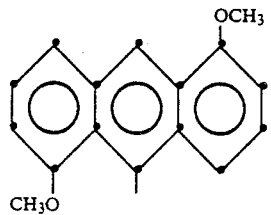,

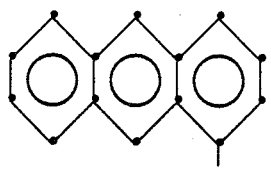,

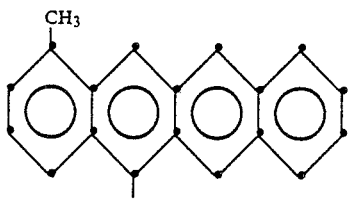,

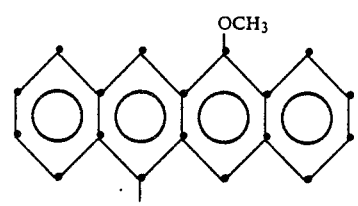,

L represents:

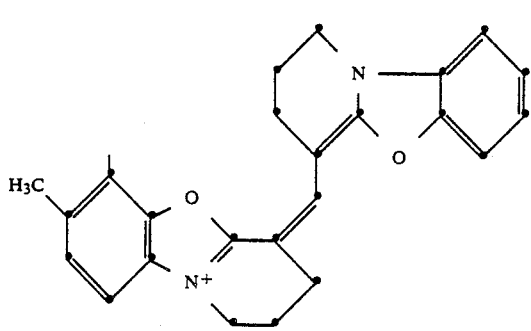

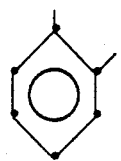;

J, R″, R‴ and R″″, taken together, represent one of the following groups:

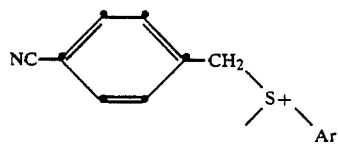

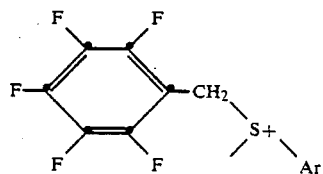

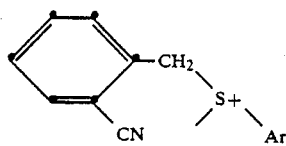

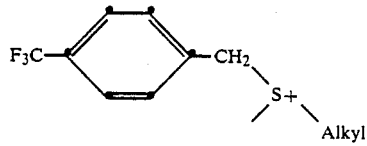

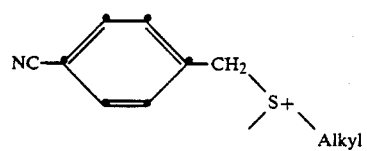

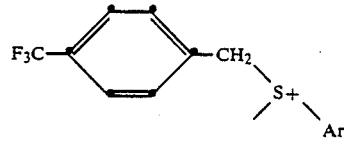

wherein Ar represents an optionally substituted aryl group; and $W^\ominus$ represents $BF_4$, $ClO_4$, $AsF_6$, $PF_6$, $CF_3SO_3$, $CH_3SO_3$, $SnCl_4$, $FeCl_4$, $BiCl_4$ or $SbF_6$.

17. A method of curing which comprises exposing to visible radiation (1) a material curable by a Bronsted acid and (2) a compound having the formula:

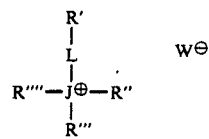

wherein:

R' represents an electron donating chromophore group which absorbs said visible radiation, and which exhibits a higher energy occupied molecular orbital than at least one of R'', R''' and R'''';

R'' represents the same substituent as R' or R''', an optionally substituted aryl group or an optionally substituted alkyl group having from 1 to 18 carbon atoms;

L represents orthophenylene;

R''' represents an electron withdrawing alkyl, aryl or heterocyclic group;

J represents an S, Se, As, N or P atom; and when J represents As, N or P, R'''' represents the same substituent as R', R'' or R''' and, when J represents an S or Se atom, R'''' represents O or an electron pair; and, W$^\ominus$ represents an anion capable of forming a Bronsted acid having a pKa of less than 7, said compound being capable, upon exposure to visible said radiation, of forming a Bronsted acid.

* * * * *